United States Patent [19]

Howard et al.

[11] Patent Number: 5,110,477

[45] Date of Patent: May 5, 1992

[54] DIALYZER CLEARANCE CHECK SYSTEM

[76] Inventors: David B. Howard, 4620 Timberlane Rd., Crystal Lake, Ill. 68675; Rodney Kenley, 816 Fairway, Libertyville, Ill. 60048; Dennis Berry, 209 S. Shannon Dr., Woodstock, Ill. 60098; Prakash Keshaviah, 10840 41st Ave., N. Plymouth, Minn. 55441; Rohit Vishnoi, 4235 Bloomington Ave., Arlington Hts., Ill. 60004

[21] Appl. No.: 479,504

[22] Filed: Feb. 13, 1990

[51] Int. Cl.$^5$ .................. B01D 61/28; B01D 61/32
[52] U.S. Cl. .................. 210/647; 210/321.65; 210/32.71
[58] Field of Search .............. 210/636, 634, 637, 644, 210/645, 646, 647, 649–652, 321.62, 321.6, 321.65, 321.71; 128/898; 422/48; 435/2, 1

[56] References Cited

U.S. PATENT DOCUMENTS 4,695,385 9/1987 Boag ........................ 210/636

*Primary Examiner*—Frank Sever

[57] ABSTRACT

A method for determining the clearance competency of dialyzers utilized in renal hemodialysis comprises measuring the conductivity of a dialysate solution of low initial conductivity while circulating a priming solution of greater conductivity on the blood side of the dialyzer, correlating the rate of dialysis of molecules contained in the printing solution to known clearance rates for urea or other targeted blood impurity for the types and compositions of the particular dialysis membranes being utilized, and calculating the precise length of treatment time or other treatment parameters required to cleanse the blood to be dialyzed of impurities and biotoxins to a predicted target value. Failsafe control means which prevents mistakes in connecting unsafe fluid sources to the dialyzer is also provided.

11 Claims, 8 Drawing Sheets

DIALYZER CLEARANCE CHECK SYSTEM

FIELD OF THE INVENTION

This invention relates to the field of hemodialysis, and more particularly, to a method for determining the clearance competency for each dialyzer unit immediately prior to use, so that adequacy of uremic toxin removal for individual patients can be ascertained.

BACKGROUND OF THE INVENTION

In the field of renal dialysis, the use of dialyzer cartridges to remove blood-borne uremic toxins and by-products of metabolism has been conventional for may years. Typically, such a cartridge contains essentially two chambers separated by a semipermeable membrane. Blood is perfused through the first chamber and returned to the patient. A dialysis solution is simultaneously circulated through the second chamber. A concentration gradient is thereby established which causes toxic molecular species contained in the blood to migrate through the semipermeable membrane and into the dialysis solution.

The principle of hemodialysis has been refined extensively. The use of a large plurality of semipermeable hollow fiber membranes in dialyzers is now utilized to greatly increase the surface area to facilitate diffusion across the membrane structure. The hollow fiber membranes are composed of a variety of materials including cellulose acetate, cellulose triacetate, polyacrylonitrile, polysulfone, and regenerated cellulose, the latter being most commonly used. These hollow fibers are small bore capillaries arranged in parallel. The bundle of fibers is typically potted in a curable sealant at both ends.

Upon cure, the embedded fibers are cut through at the ends to expose the bores of the fibers, as disclosed in U.S. Pat. No. 4,227,295 (Bodnar et al). The fiber bundle is then enclosed in a housing which forms the dialysate chamber. Examples of dialyzers of this construction together with the mechanical details as to closure, inlet and outlet ports, and the like are illustrated in U.S. Pat. No. 4,283,284 (Schnell) and U.S. Pat. No. 4,600,512 (Aid).

In the operation of the dialyzer, patient blood is pumped through the hollow fiber bundle, and a dialysis solution is pumped through the dialysate chamber so that dialysis solution constantly bathes the exterior hollow fiber surfaces. Pump assisted movement of blood through the dialyzer is required in order to displace a sufficient volume for effective cleansing within a treatment time of less than six hours. Another pump propels dialysis solution through the dialysate chamber and also regulates by valves under microprocessor control, the proper mixing of dialysis solution concentrate and water. Electrolyte concentrations are monitored by continuous conductivity measurement. Another function of this pumping device is to carefully control fluid back pressure so as to prevent excessive water loss form the blood.

It is also important to control loss of sodium to the dialysis solution during treatment so as to avoid dialysis disequilibrium syndrome, a condition thought to result from a too rapid reduction in salt concentration from about 145 mEq/liter prior to treatment, to 134 mEq/liter after treatment. Various methods of changing the salt content of the dialysis solution during treatment to avoid an abrupt reduction in sodium have been proposed, as in U.S. Pat. No. 4,722,798 (Goss).

Other medically adverse effects upon patients undergoing dialysis may result from an inadvertent failure to completely dialyze the patient. At the present time, the average dialysis patient has a life expectancy of only about five years. One reason these patients tend to have a short life expectancy is the deleterious effect of a chronic buildup of various toxins that either are not eliminated at all, i.e. do not pass through the hollow fibers, or are not completely reduced to nontoxic levels. The identity of many of these supposed toxins is not known, although those species known to be eliminated in urine, such as creatinine, urea, phosphate, hydrogen ions, etc. are associated with serious medical consequences when permitted to accumulate in excess of normal levels.

It is common practice in the field of hemodialysis to reuse dialysis cartridges. There is technology available for cleaning, disinfecting, or sterilizing used dialysis cartridges. (See, for example U.S. Pat. No. 4,695,385). Eventually, however, the cartridge must be discarded because it loses its dialyzing competency. At the present time, the competency of dialyzers is not being rigorously monitored, and a dialyzer is discarded when it visually appears unclean after recleaning, or when fiber bundle volumes and ultrafiltration rates become normal. It is now known that severe dialyzer dysfunction can occur even when appearance, total cell volumes and ultrafiltration rates are normal, as reported by Delmez et al., "Severe dialyzer dysfunction during reuse," *Kidney International*, 35:244 (1989). It is also known that dialyzer competency can not be accurately predicted by the age of the dialyzer of the number of uses.

One measure of adequacy of dialysis for the individual patient as to a particular dialyzer is calculated from the following equation:

$$KT/V \gtrsim 0.8$$

wherein V is an expression of the volume of distribution of urea which is approximately equal to total body fluid volume derived for each individual patient from data such as height, weight, and sex, K is the urea clearance of the dialyzer in use in ml of blood totally cleared in urea each minute, and T is the treatment time. A typical product insert accompanying a dialyzer unit contains a graph of urea clearance versus blood flow rate obtained by random testing of a sample of dialyzers from a particular manufacturing lot. Upon incorporating these values into the above equation, the minimum treatment time can be calculated for a given KT/V value. Other parameters that may be varied to achieve adequate dialysis include blood flow rate, dialysis solution flow rate, dialyzer competency, and temperature.

It has been determined empirically that KT/V values of about 0.8 or greater are associated with low levels of morbidity. See Gotch, L A., Sargent, J A., *Kidney Int.*, 28: 526–537, 1985. Even in the use of new dialyzer units there is some risk that a unit selected from a particular lot will have a significantly lower K value than the value depicted by the product insert graph. The patient receiving treatment from such a unit is therefore at risk of being under-dialyzed. The likelihood of under-dialysis increases upon reuse of the dialyzer because of the unpredictability of loss of dialyzer competence.

SUMMARY OF THE INVENTION

It is an object of the present invention to provide a method for conveniently determining the clearance competency of dialyzers immediately before each use so that treatment parameters may be varied to achieve adequate dialysis. A further object of this invention is to provide a failsafe test apparatus for performing such determinations. The present method comprises circulating a priming fluid containing a solute through the blood side of a dialyzer, simultaneously circulating a diffusion fluid containing a lower level of such solute through the dialysate chamber, measuring the level of the solute in the diffusion fluid as the two fluids are circulated on opposite sides of the semi-permeable membrane, correlating the concentration of the solute appearing in the diffusion fluid to the clearance of urea or another standard reference substance and varying treatment parameters to ensure adequacy of dialysis. In a further step, the presence of dialysis solution in the dialysate chamber is verified prior to commencement of hemodialysis.

Apparatus is also provided in the verification step which comprises detecting means capable of identifying blood in the circulation pathway on the blood side of a dialyzer, which, when combined with measuring means for determining the composition of a diffusion fluid, control means for activating a blood displacing pump to circulate blood through the dialyzer, and interfacing means for disabling the blood displacing pump when dialysis solution is not present in the dialysate chamber of the hemodialysis machine prevents blood from being dialyzed against an nonphysiological solution.

DETAILED DESCRIPTION OF THE PREFERRED EMBODIMENT

In the practice of the present method, a priming fluid is introduced into the blood circulating lines of a hemodialysis dialyzer unit and circulated through the lines utilizing the blood displacing pump which ordinarily pumps patient blood. This fluid contains a solute molecule capable of diffusing through the semipermeable membrane of the dialyzer. A diffusion fluid is circulated on the dialysate side of the dialyzer. Since the dialyzer membrane acts as a sieve in retaining large molecular weight molecules such as blood proteins while allowing lower molecular weight substances to pass through the membrane, the solute is chosen to be of low molecular weight with diffusion properties similar to urea. Although urea is but one of many substances removed from blood by dialysis, urea clearance has become a standard reference for dialyzer competency. Thus a solute molecule should preferably be of a similar molecular weight to urea. It should also be a substance which is easy to standardize, and preferably for which a sterile, commercial, and physiologically compatible source is available. The preferred solute is sodium chloride, at a preferred concentration about 0.9 percent, but other salts such as potassium chloride or lithium chloride can be substituted. Uncharged small molecules may potentially be utilized. Urea, however, is not preferred because of the difficulty of measurement in the field.

Other substances normally eliminated from blood by the kidneys or through hemodialysis having different diffusion properties than urea may also be selected. The KT/V expression would then apply to the K clearance value for that substance. If the substance itself can not be utilized in the K determination, then a molecule of similar molecular weight and diffusion properties is to be substituted. Examples of alternative substances to urea include creatinine, hydrogen ions, inorganic phosphate, and cyanocobalamin.

Figure 1:
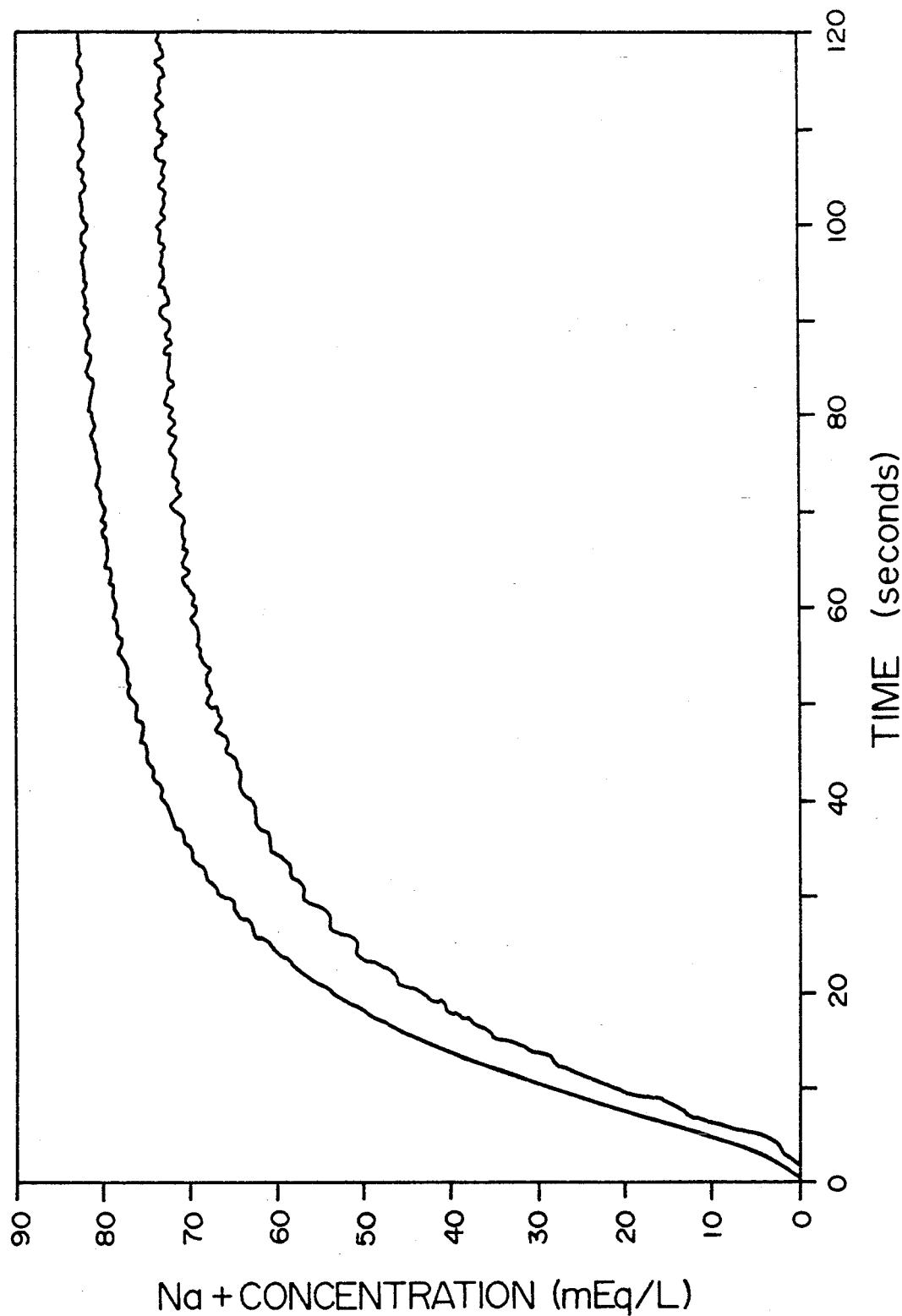
FIG. 1 is a rectilinear plot showing the comparative clearances of sodium of two different dialyzers of similar composition.

As soon as the priming fluid contacts the semipermeable membrane of the dialyzer, the solute begins to diffuse across the membrane into the diffusion fluid. The solute increases in concentration in the diffusion fluid as a function of time. FIG. 1 of the drawings illustrates the typical kinetics of diffusion of two dialyzers having different K values. The dialyzer diffusion curve shows a higher level of solute after equilibration, for the dialyzer membrane having the higher K value. Equilibration occurs when the rate of diffusion across the membrane into the dialysate chamber is equal to rate leaving with the dialysate. Such equilibration occurs because, unlike a static system of passive diffusion, a dialysis system involves the countercurrent flow of dialysate and priming fluid, so that the concentration of the solute in the diffusion fluid is always a fraction of its concentration in the priming solution. For a review of the mass transfer properties of various solutes in dialysis, see *Clinical Dialysis*, ed. Nissenson et al., Appleton, Century, Crofts, 1984.

The ultimate steady state equilibrium value is directly proportional to the rate of solute diffusion. Measurement of solute concentration at unit time to obtain a rate value extrapolatable to the final solute level at equilibrium, is an alternative to measuring at equilibrium.

The diffusion fluid may be any solution containing a lower concentration of solute than the priming solution, which also does not contain any substance which distorts the mass transfer properties of the solute. The concentration of solute in the diffusion fluid must be less than the range of its expected concentration after the diffusion test. A relatively large concentration gradient should be selected from at least a concentration ratio of 10:1 to infinity. Accordingly, the preferred diffusion fluid is water.

Clearance of the solute may be measured in alternative ways. For example, the priming and diffusion fluids may be circulated concurrently or in a countercurrent fashion. One of both fluids may be in a recirculation loop. Alternatively, flow of either fluid may be interrupted while the other fluid is flowing continuously or in a recirculating loop. Accordingly, solute concentration may be measured downstream of the dialyzer on either side where flow is occurring to obtain a value correlatable to urea clearance. Finally, in the most generalized system, priming fluid contacts the blood side of the dialyzer membrane, diffusion fluid simultaneously contacts the dialysate side of the membrane and measurement of changes in the solute level on either side is correlated to a corresponding standard reference substance clearance value. In the preferred method, however, the solute concentration at equilibrium is measured in the diffusion fluid while both priming fluid and diffusion fluid are flowing continuously.

Diffusion of solute across the dialysis membrane may be monitored to equilibrium by appropriate measuring means, or be measured once after a period of time determined empirically to be sufficient for equilibrium to be established. The measuring means is selected in accordance with the particular solute utilized. In the case of sodium chloride, an in-line conductivity meter can conveniently measure the conductivity of equilibrated diffusion fluid circulating through the dialysate chamber. Alternatively, such conductivity meter can measure the depleted level of solute contained in the priming solution circulating through the dialyzer in a loop. Other suitable measuring means include spectrophotometers for solutes having characteristic wavelengths of optical absorption, as for example, in the colorimetric determination of cyanocobalamin, ion specific electrodes for measuring corresponding ionic solutes, and fluorophotometers for solute molecules conjugated to fluorophores.

Correlation of the levels of test solute measured in the diffusion fluid with corresponding predicted urea or other standarized clearance values is obtained empirically. A number of dialyzers composed of different materials are tested for clearance of sodium chloride and bovine urea. Mass transfer area coefficients ($K_oA$) are calculated for both sodium and urea. The linear regression parameters are then determined to predict blood urea $K_oA$ from the sodium $K_oA$. The urea clearance at various blood flow rates may then be calculated from the urea $K_oA$. The tests are conducted at a high flow rate (e.g. 400 ml/min.) which provide correlate values applicable to lower flow rates with good accuracy. The measurable differences between dialyzers are thereby enhanced. In the case of sodium chloride the correlation between predicted and actual urea clearance values if 0.992. This means that once a K value is obtained for sodium clearance at the time of treatment, its urea correlate can be read from a conversion table constructed from the regression plots. The $K_{urea}$ value can then be substituted in the expression KT/V. Treatment parameters, e.g. blood flow rate, treatment time, dialyzer type, etc. may then be varied to ensure adequacy of dialysis.

In proceeding with hemodialysis immediately following K determination, there is a risk of error in failing to replace diffusion fluid with properly constituted dialysis solution which could lead to severe adverse effects to the patient. It is therefore desirable to provide a failsafe system which prevents the blood displacing pump from being activated to pump blood unless the presence of properly proportioned dialysate in the dialysate chamber is verified. Thus, in an alternative embodiment of the present method, the determination of $K_{urea}$ is followed by the additional step of verifying the presence of dialysis solution in the dialysate chamber before pumping of blood is allowed to proceed.

Since the dialysate has a different composition than the diffusion fluid, measuring means can distinguish between them. For example, in the use of sodium chloride as solute, a conductivity meter is utilized to measure the concentration thereof in the diffusion fluid. A similar conductivity meter is also utilized to monitor the dilution of dialysis solution during treatment.

The nonpermissive state, i.e. the presence of blood on the blood side of the dialyzer in conjunction with the presence of diffusion fluid in the dialysate chamber, is detected by detecting means positioned in the blood circulation lines. Such detecting means may be a densitometer, nephelometer, or any other instrument capable of detecting translucence of opacity of otherwise distinguishing between blood and a clear solution. The signal output of the measuring means and detecting means is connected to control means such as a microprocessor which interprets the signals. The control means also has a signal output connected to an interfacing means for activating the blood displacing pump. Such interfacing means may be a relay diode, a resetable fuse, or switching circuit which prevents electric current from activating the pump motor upon receipt of a positive signal from the control means. Thus, a positive signal generated by the detecting means also generates a positive control signal thereby disabling the blood displacing pump in any situation wherein the control means receives a conductivity signal below a predetermined level. The risk of dialyzing a patient's blood against a nonphysiological medium is thereby greatly reduced.

Figure 2:
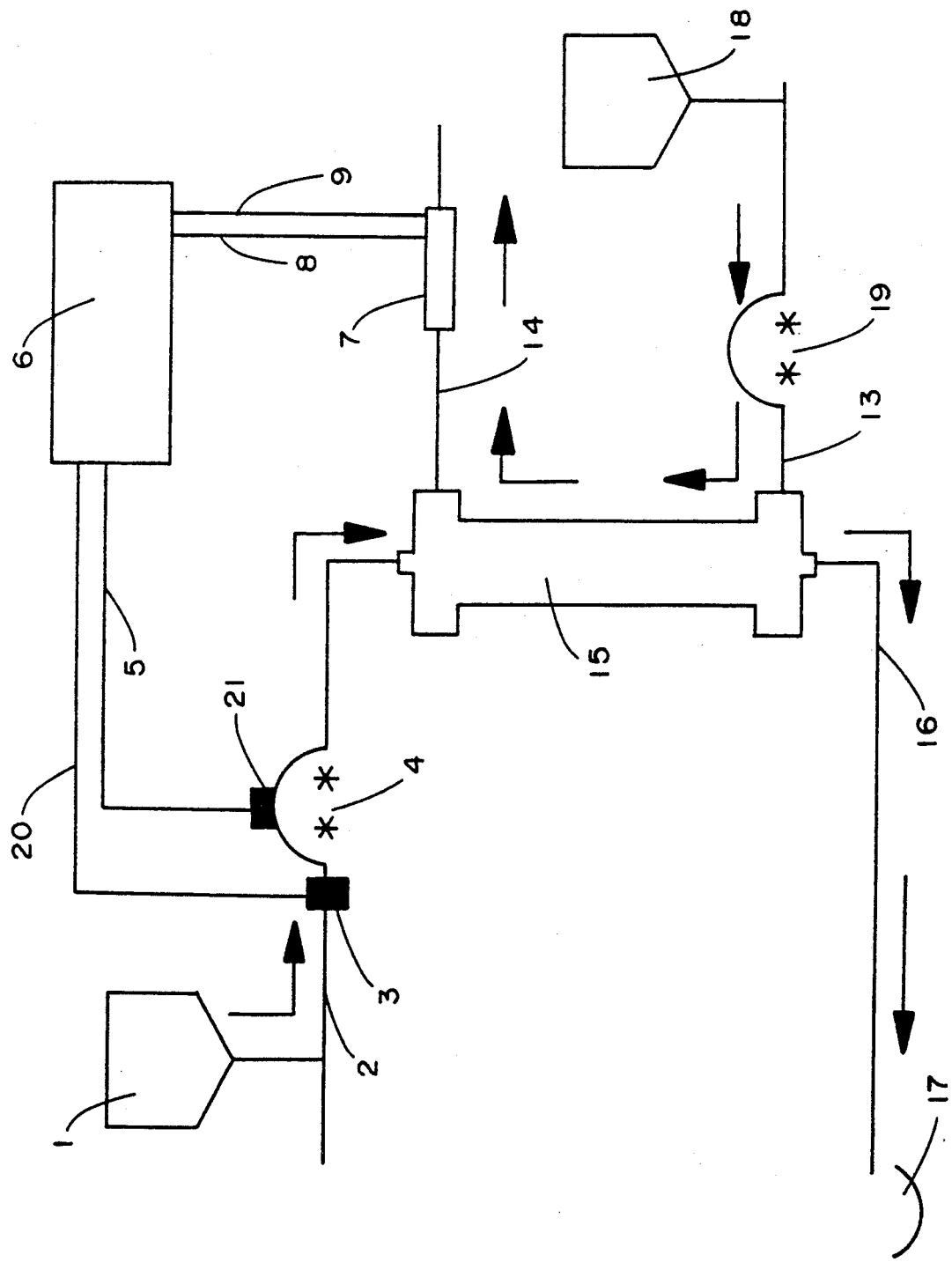
FIG. 2 is a schematic showing the components of an apparatus for carrying out the present method.

Referring to the drawings, FIG. 2 is a schematic illustrating the components of the preferred apparatus. Priming solution contained in a priming solution reservoir 1 is pumped by a blood pump 4 through an inlet line 2 to a test dialyzer 15. A blood detecting means 3 is situated in-line of the inlet 2. Priming fluid flows through a plurality of hollow fiber membrane tubules (not shown) contained in test dialyzer 15 and exits to a drain 17 through a return line 16. Simultaneously, diffusion fluid contained in a diffusion fluid reservoir 18 is pumped by a dialysate pump 19 through a dialysate inlet line 13 to the test dialyzer 15, and flows through the dialysate chamber thereof, so as to establish a steady state equilibrium level of solute on the dialysate side of the hollow fiber membrane tubules. Diffusion fluid exiting the test dialyzer 15 through an outlet line 14 passes through measuring means 7 such as a conductivity meter.

Control means 6, which may be an electronic microprocessor, is connected to the blood detecting means 3 via signal transmitting means 20, such as ordinary computer wire. Similarly, the control means 6 is connected to the measuring means 7 via signal transmitting means 8.

An analog electronic signal generated by the blood detecting means 3 or the measuring means 7 and transmitted to the control means 6 by the signal transmitting means 20 and 8 respectively is conventionally processed, as by digital conversion. Control settings for digital limits as to each converted input signal are conventionally programmed into the memory of the control means 6. In the event that the digital value for the converted input from the detecting means exceeds its preset limit, and simultaneously the digital value for the converted input from the measuring means 7 is less than its preset limit, an output signal is generated by the control means 6 and transmitted via a output signal transmitting means 5 to pump disabling means 21, which results in an electrical or mechanical disablement of the blood pump. It is also desirable to monitor the temperature of the dialyzing solution, as with a thermistor, so that a temperature correction may be made in computing the proper conductivity. A thermistor may conveniently be situated within the flow cell of the measuring means 7, and is connected to the control means 6 via a thermistor transmitting means 9. Such transmitting means may be ordinary electrical wire.

Other advantages of the present invention will be apparent from the Examples which follows.

EXAMPLE 1

A model for prediction of urea clearance (UR) was developed in a four stage procedure. In stage one, dialyzers were classified into three groups: cellulose acetate dialyzers, Cuprophan ® dialyzers, and dialyzers of high permeability composition. In stage two, sodium (NA) clearance (K) is determined at a blood side flow rate of 400 ml/min. (Qb), dialysate side flow rate of 500 ml/min. (Qd), and a ultrafiltration rate less than ±10 ml/min. From this data, the mass transfer area coefficient ($K_oA$) for sodium is estimated as:

$$K_oA(NA) = Qb\,(1 - Qb/Qd)^{-1}\log_e\frac{1 - K_{NA}/Qd}{1 - K_{NA}/Qb} \quad (1)$$

In stage three the urea mass transfer area coefficient is predicted in the following equations:

$$\begin{aligned}K_oA(UR) =\ & 35.806 + 0.901*K_oA(NA) \quad (2)\\ & \text{if the dialyzer is cellulose acetate}\\ & 67.002 + 0.706*K_oA(NA)\\ & \text{if the dialyzer is Cuprophan \textregistered}\\ & 191.979 + 0.484*K_oA(NA)\\ & \text{if the dialyzer is of high}\\ & \text{permeability composition.}\end{aligned}$$

In stage four the urea clearance at ultrafiltration less than ±10 ml/min. is predicted according to the following equation:

$$K_{UR} = \frac{Qb_w Qd}{Qb_w - Qd}\ \frac{1 - \exp[(1 - Qb_w/Qd)Qb_w^{-1}K_oA(UR)]}{\exp[(1 - Qb_w/Qd)Qb_w^{-1}K_oA(UR)]} \quad (3)$$

where $$Qb_w = Qb[(Hct*.72) + (1 - Hct)*.93]$$

is the adjusted blood water flow rate and Hct is the hematocrit.

When this procedure was applied to the data, an extremely high degree of concordance was achieved between the predicted urea clearance and the actual measured urea clearance (r=0.992).

Figure 3A:
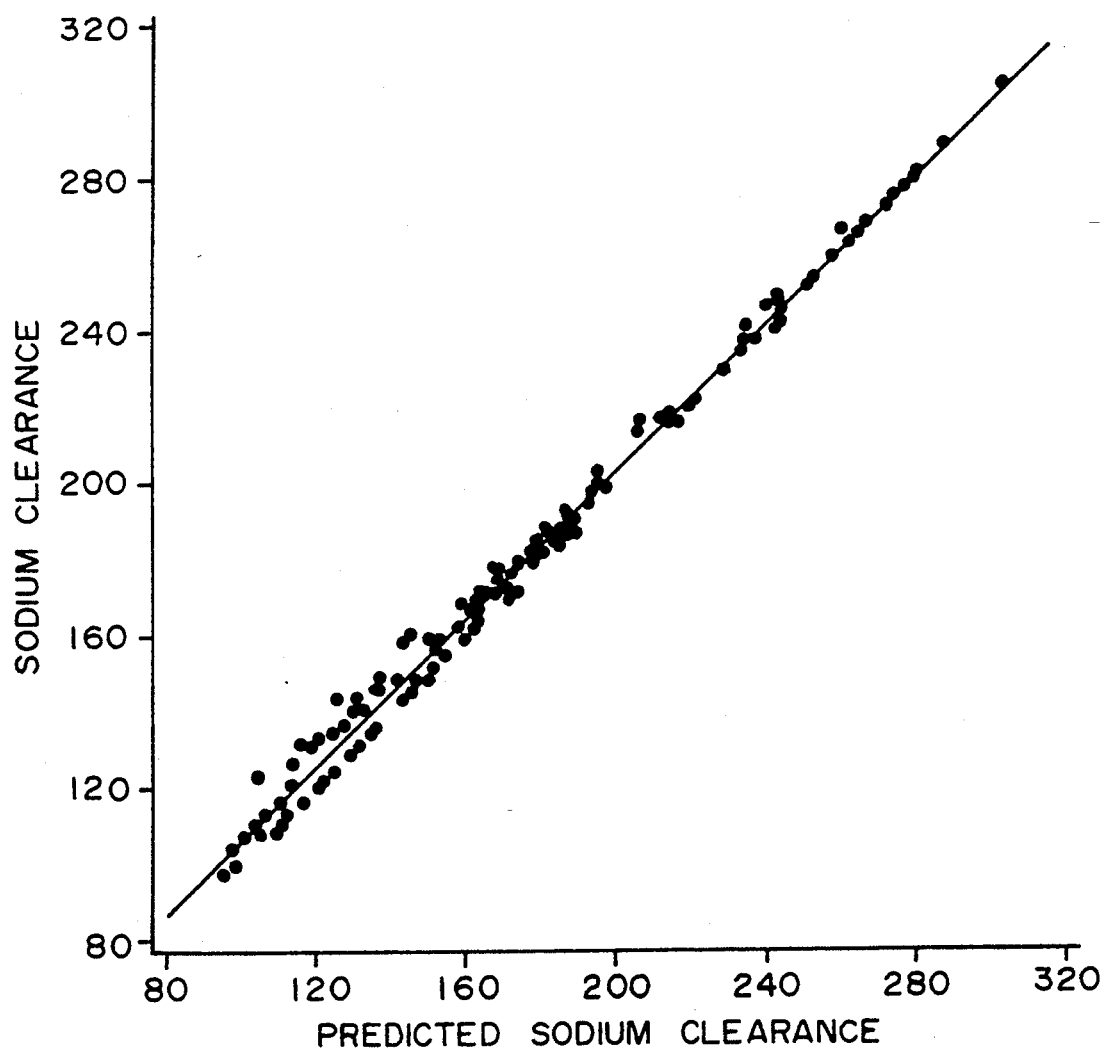
FIG. 3a is a graph of predicted and experimental sodium clearance values.

Using equation 1 above, the sodium mass transfer area coefficient can be estimated for several blood flow rates. However, a more accurate determination of $K_oA$ can be made at the higher flow rates, e.g. 400-500 milliliters per min. This is because at higher blood rate rates, differences between dialyzers are more pronounced than at lower blood flow rates. If either Qb or clearance is measured inaccurately, the resulting value for $K_oA$ would be biased. To verify the accuracy of the derived value of $K_oA$ clearances at lower blood flow rates, clearances were predicted using equation 3. The predicted clearances had good correlation with actual measured clearances, as shown in FIG. 3a.

To predict urea clearance, one can use equation 3 if there exists a reasonable estimate of $K_oA$ for urea. Three approaches to estimating $K_oA$ for urea were investigated: (1) equate $K_oA(UR)$ to $K_oA(NA)$, (2) predict $K_oA(UR)$ from $K_oA(NA)$ via linear regression and (3) predict $K_oA(UR)$ from $K_oA(NA)$ via linear regression within each family of dialyzers. Three families of dialyzers were identified in this study as (i) cellulose acetate membrane dialyzers, (ii) Cuprophan ® membrane dialyzers, and (iii) high permeability types of dialyzers belonging to one of the following: AN69, CT110G, CT190G, and F60.

The predictive equations for estimating $K_oA(UR)$ from $K_oA(NA)$ using the all three of these three approaches are summarized in Table 1.

TABLE 1

| Approach | Approaches for Predicting $K_oA$(UREA) | | |
|---|---|---|---|
| | Prediction Equation | Family | $R^2$ |
| (1) | $K_oA(UR) = K_oA(NA)$ | all | NA |
| (2) | $K_oA(UR) = 76.511 + 0.703\,K_oA(NA)$ | all | 0.9017 |
| (3) | $K_oA(UR) = 35.806 + 0.901\,K_oA(NA)$ | Cellulose Acetate | |
| | $= 67.002 + 0.796\,K_oA(NA)$ | Cuprophan ® | 0.9963 |
| | $= 191.979 + 0.484\,K_oA(NA)$ | Other | |

Figure 3B:
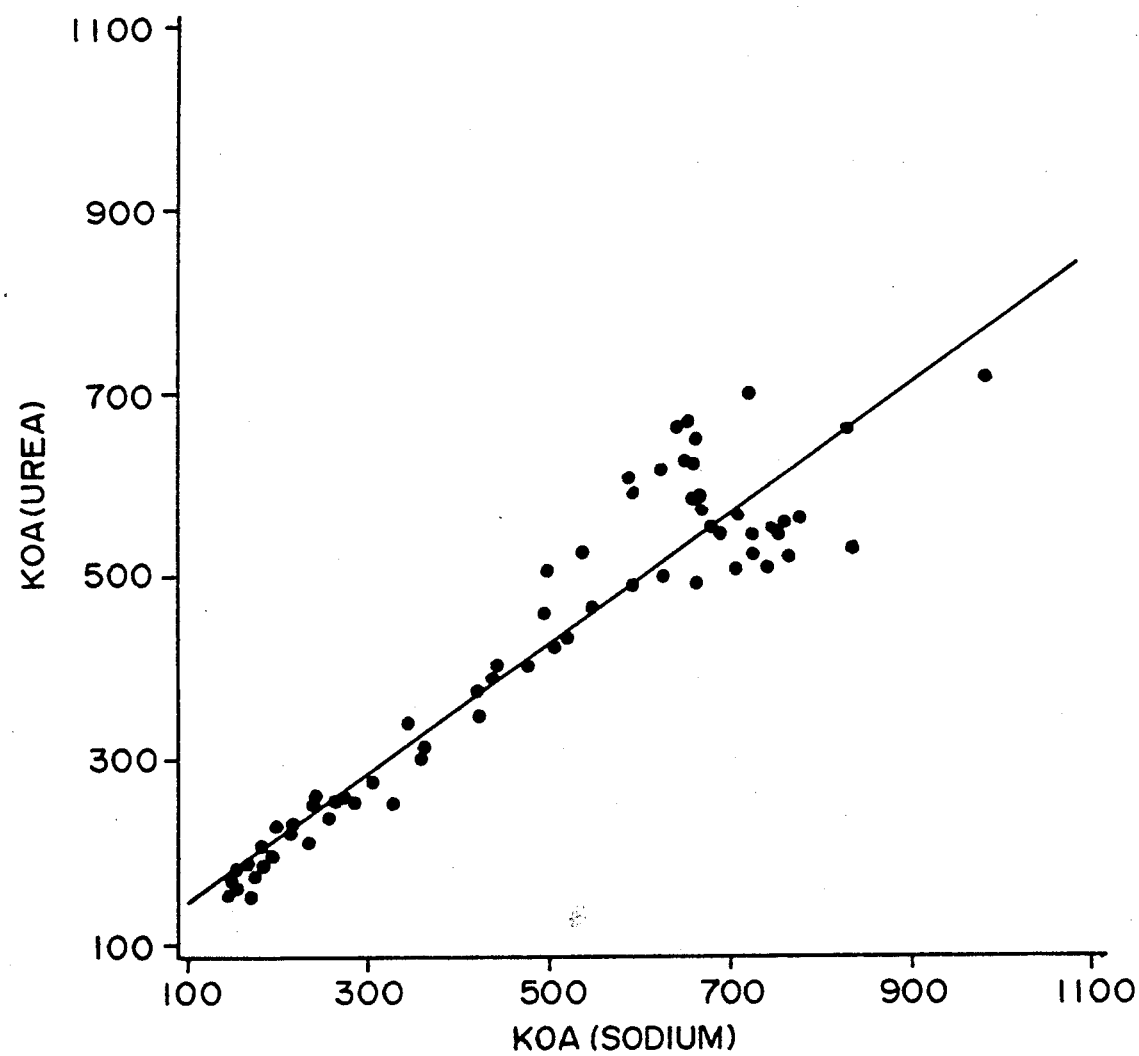
FIG. 3b is a regression plot of urea mass transfer values as predicted by sodium clearance.
Figure 3C:
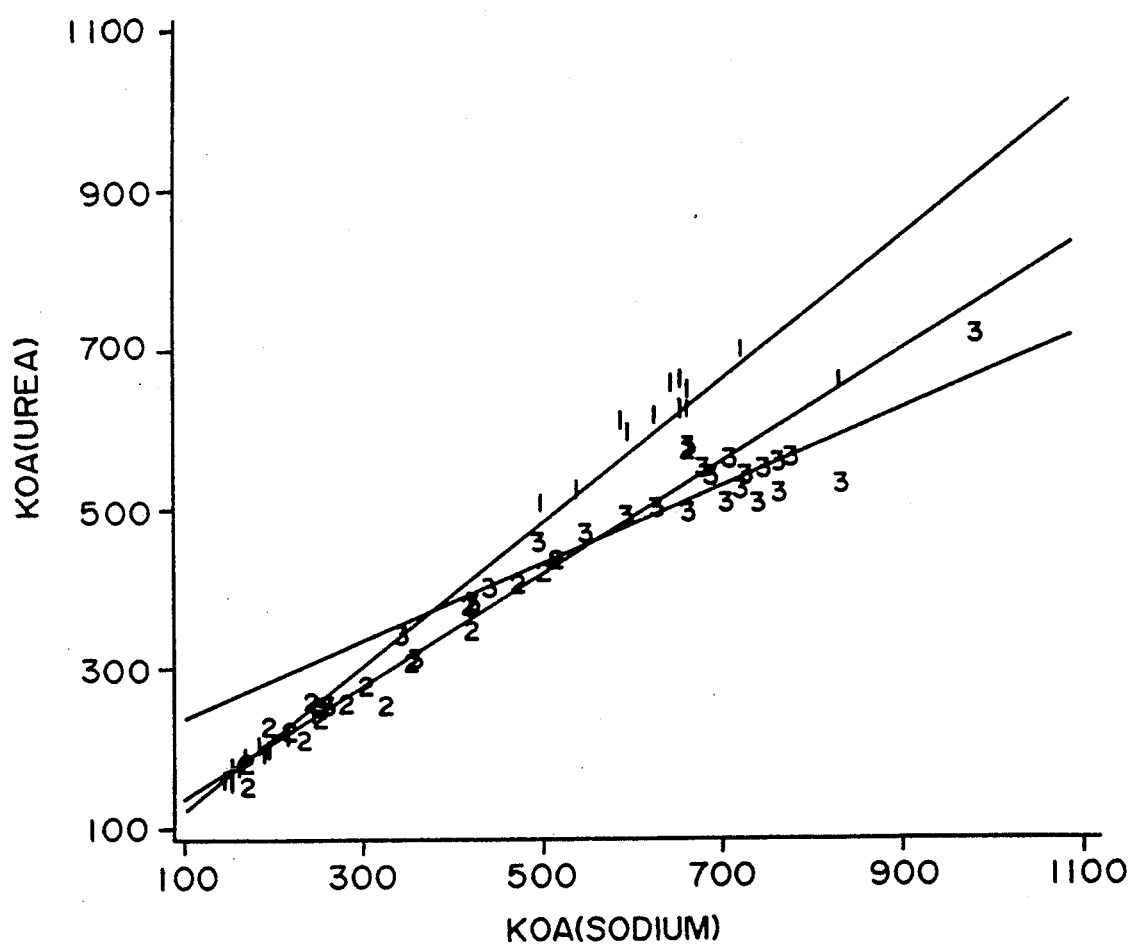
FIG. 3c is a regression plot of urea mass transfer values as predicted by sodium mass transfer values for each family of dialyzers.

The regression lines for the second and third approaches are graphically illustrated in FIGS. 3b and 3c, respectively.

Using the predicted values of $K_oA(UR)$ in conjunction with (equation 3), urea clearances were predicted and compared to the actual clearances. The results are presented in Table 2, FIGS. 4a, 4b, and 4c.

TABLE 2

| | Comparison of Actual vs. Predicted Urea Clearance | | |
|---|---|---|---|
| $K_oA$(UREA) determined from | Regression line of Actual vs. Predicted Clearance | Pearson's Correlation | Concordance Correlation* |
| Approach (1) | Actual = 54.904 + 0.690*Predicted | .922 | .881 |
| Approach (2) | Actual = −5.49 + 1.023*Predicted | .982 | .980 |

TABLE 2-continued

Comparison of Actual vs. Predicted Urea Clearance

| $K_oA(UREA)$ determined from | Regression line of Actual vs. Predicted Clearance | Pearson's Correlation | Concordance Correlation* |
| --- | --- | --- | --- |
| Approach (3) | Actual = −0.85 + 0.9996*Predicted | .992 | .992 |

*The Concordance Correlation measures the degree to which the predicted urea clearance agrees with the actual urea clearance. Perfect agreement (a concordance correlation of 1) occurs when the Pearson correlation equals 1 and the linear relationship is given by: Actual = 0 + 1*Predicted.

Figure 4A:
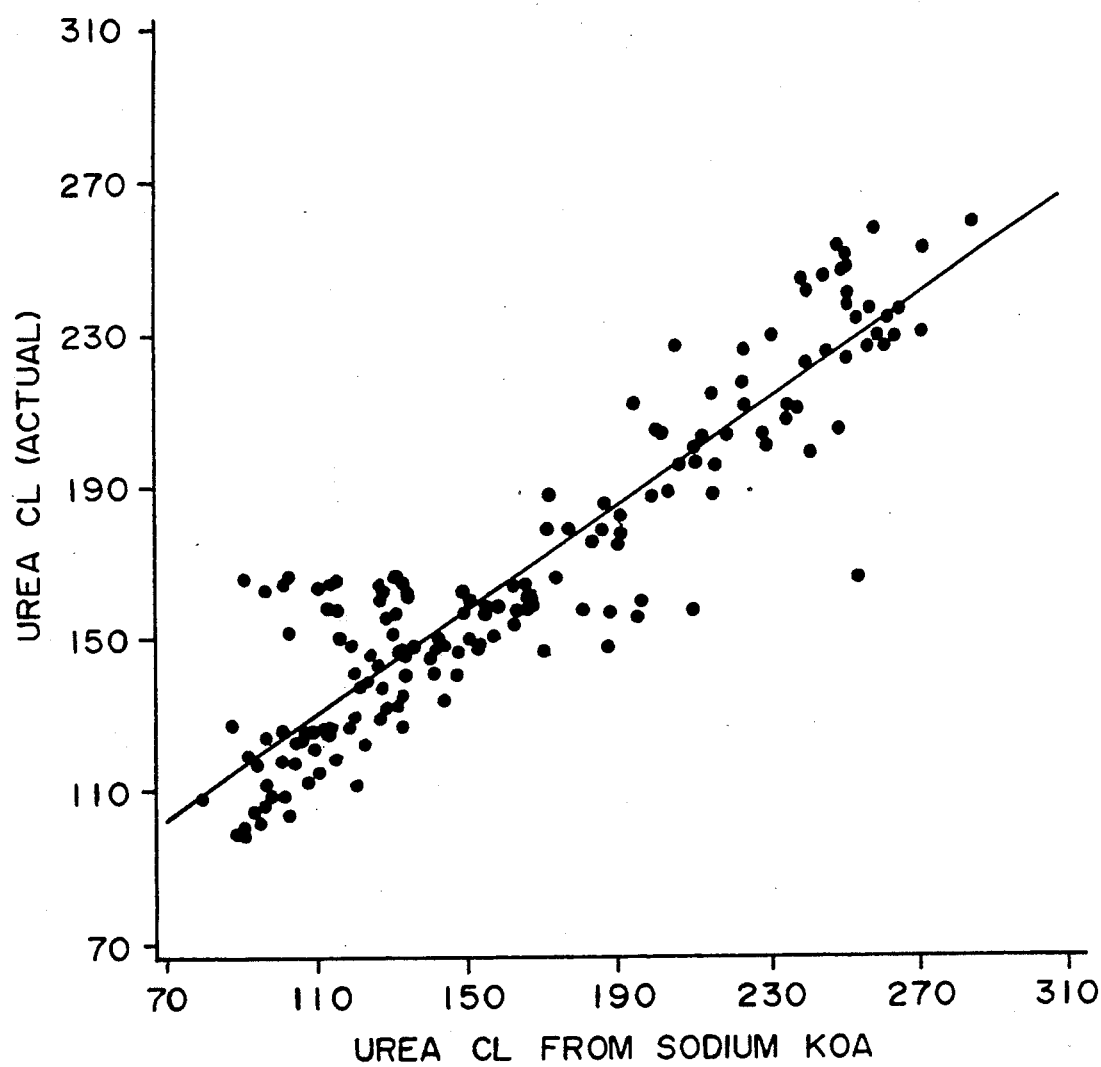
FIG. 4a is a graph showing predicted and experimental urea clearance.

FIG. 4a compares the actual urea clearance for all dialyzers versus the urea clearance one would predict based on a $K_oA(UR)$ determined using approach (1). The concordance correlation, which measures the degree of concordance or perfect agreement between actual vs. predicted clearance, was only 0.881 for this approach (the Pearson correlation coefficient was 0.922).

Figure 4B:
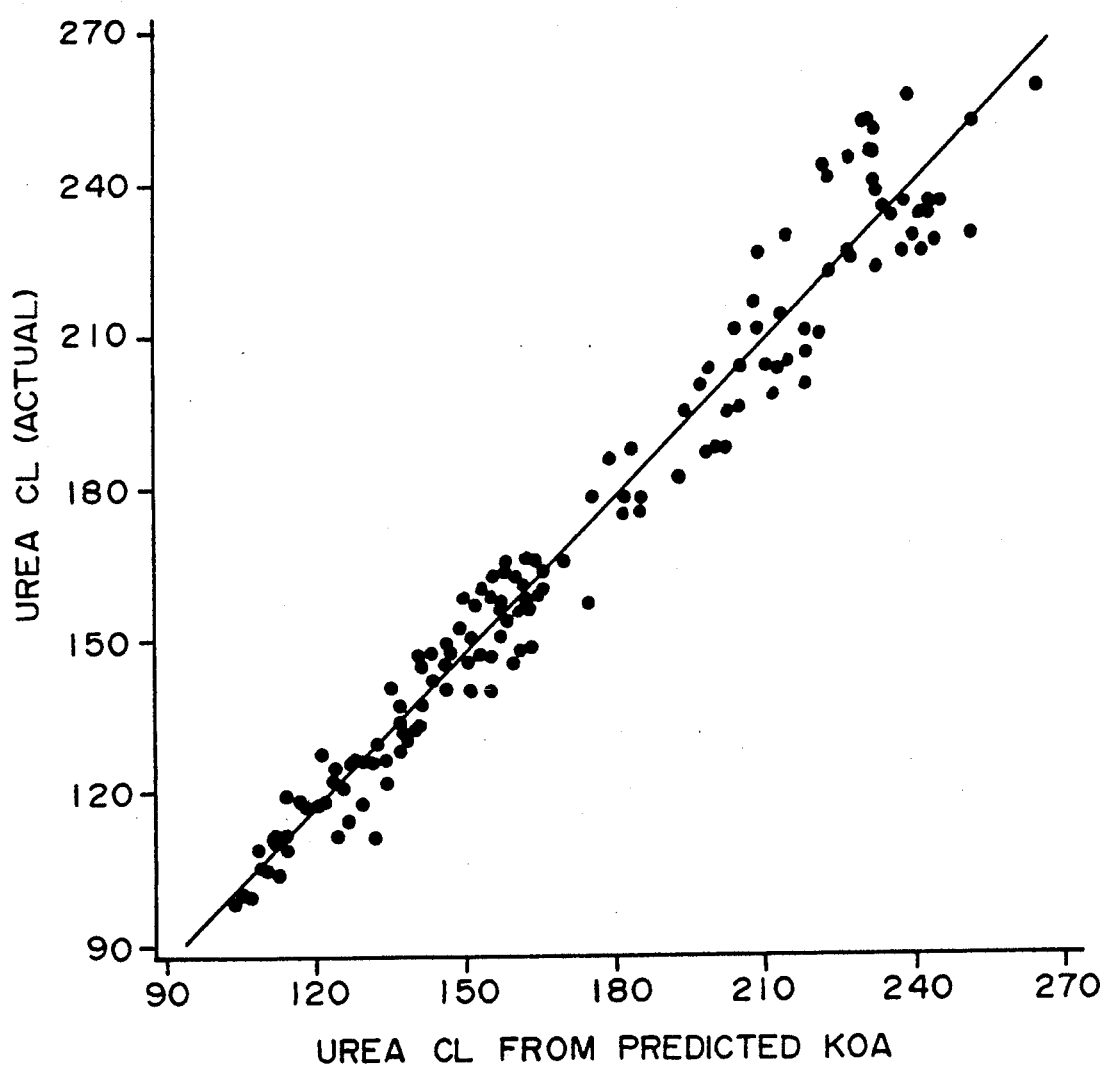
FIG. 4b shows predicted and experimental urea clearance across all families of dialyzers.

FIG. 4b compares the actual versus predicted urea clearance one would obtain when basing $K_oA(UR)$ on approach (2). Here the concordance correlation is estimated to be 0.980 with a Pearson correlation coefficient of 0.982. Hence using approach (2) to estimate $K_oA(UR)$ provides a much better method for predicting urea clearance than using approach (1).

Figure 4C:
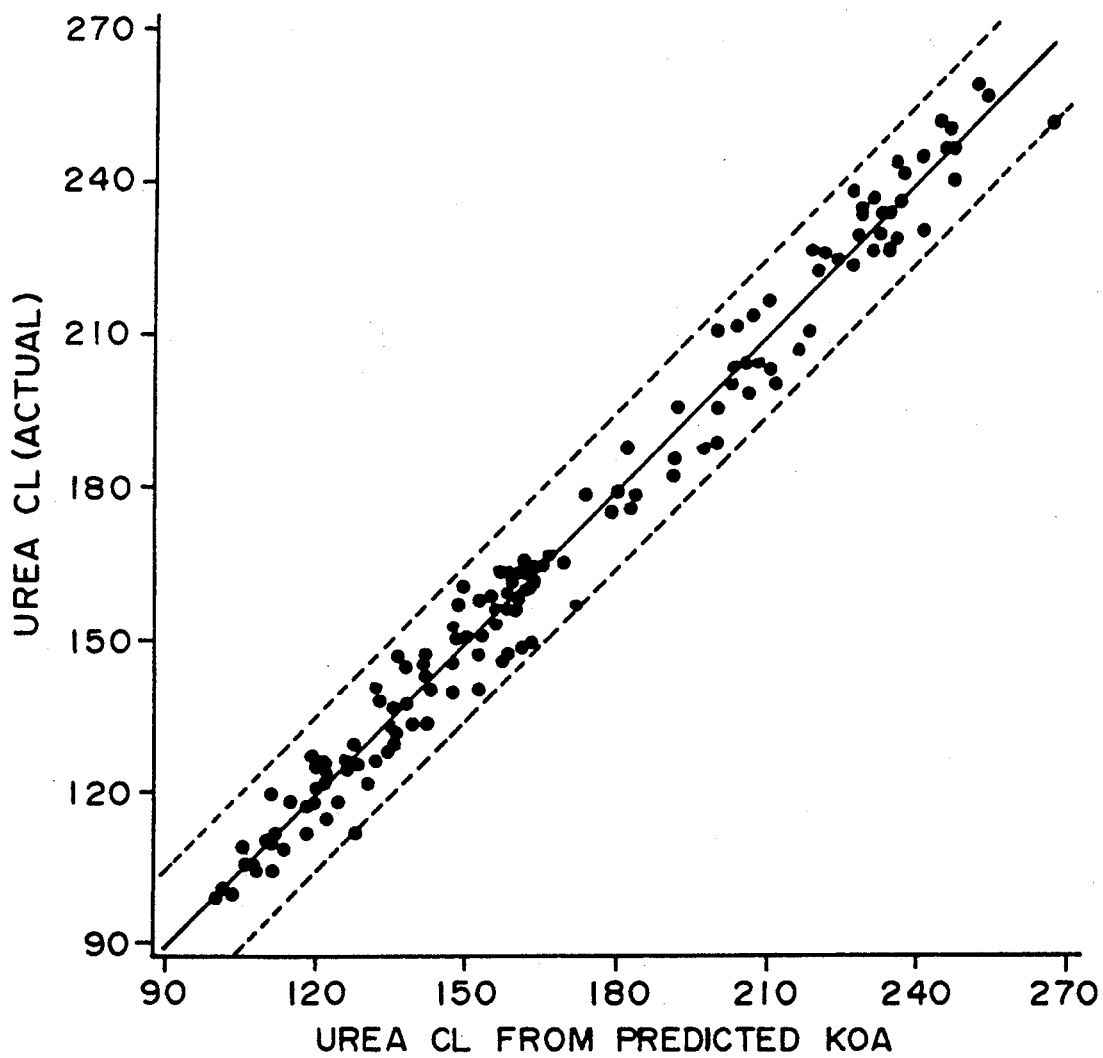
FIG. 4c shows predicted and experimental urea clearance by each family of dialyzer.

Finally, FIG. 4c compares the actual urea clearance versus the predicted urea clearance using a $K_oA(UR)$ determined from approach (3). This approach clearly gave the best agreement between actual versus predicted urea clearance with both the concordance correlation and Pearson correlation being 0.992. FIG. 3C also depicts a 99% tolerance band within which one can be 95% confident that 99% of all actual values will lie when predicted from sodium mass transfer data.

EXAMPLE 2

A 150 lb, 68 inch tall male patient presented at the clinic for hemodialysis. The V value read from a monogram was 40,000 ml. The product insert for the ST 25 dialyzer gave a K value of 241 ml/min. at a Qb value of 300. Substituting these values in the equation KT/V=1.2, and rearranging, gave a total dialysis time of 199 minutes.

Measurement of the actual K value, utilizing the present method, indicated a K value of only 173 ml/min. The calculated KT/V value for a treatment time of only 199 minutes is 0.86, indicating this patient would have been significantly underdialyzed.

Substituting the actual K value, as determined by the present method, into the KT/V expression projected a proper treatment time of 277 minutes instead of 199 minutes for this dialyzer.

That which is claimed is:

1. A method comprising determining clearance competency of hemodialyzers comprising:
   a) contacting the blood side of a dialyzer membrane with a priming fluid;
   b) simultaneously contacting the dialysate side of a dialyzer membrane with a diffusion fluid;
   c) measuring the changes in solute level on either side of the said membrane with means for measuring; and
   d) correlating the changes in solute level to a corresponding standard reference substance clearance value with means for correlating.

2. The method of claim 1 together with the further step of verifying the presence of dialysate in the dialysate chamber prior to commencement of hemodialysis.

3. The method of claim 1 wherein said solute is a molecule having substantially the same diffusion properties as a selected standard reference substance.

4. The method of claim 1 wherein said solute is a solution of sodium chloride.

5. The method of claim 1 wherein said diffusion fluid is water.

6. The method of claim 1 wherein said standard reference substance is urea.

7. A method comprising determining clearance competency of hemodialyzers comprising:
   a) circulating a priming fluid containing a solute through the blood side of a dialyzer;
   b) circulating simultaneously a diffusion fluid containing a lower level of said solute through the dialysate chamber on said dialyzer;
   c) measuring the level of said solute in the diffusion fluid after the levels of said solute in the two fluids have come to equilibrium with means for measuring; and
   d) correlating the level of said solute to a corresponding standard reference substance clearance value with means for correlating.

8. A method comprising determining clearance competency of hemodialyzers comprising:
   a) circulating a priming fluid containing a solute through the blood side of a dialyzer;
   b) circulating simultaneously a diffusion fluid containing a lower level of such solute through the dialysate chamber on said dialyzer;
   c) measuring the solute concentration at unit time to obtain a rate value extrapolatable to the final solute level at equilibrium with means for measuring; and
   d) correlating the final solute level to a corresponding standard reference substance clearance value with means for correlating.

9. A method comprising determining clearance competency of hemodialyzers comprising:
   a) circulating a priming fluid containing a solute in a loop through the blood side of a dialyzer;
   b) circulating simultaneously a diffusion fluid containing a lower level of such solute through the dialysate chamber on said dialyzer;
   c) measuring the level of solute in the diffusion fluid successively to determine the rate at which the concentration of solute diminishes with means for measuring; and
   d) correlating the rate of change in the solute level to a standard reference substance clearance value with means for correlating.

10. Apparatus for use during hemodialysis treatment with a dialyzer having a blood circulation pathway on one side of a semipermeable membrane and a dialysate chamber on the other side of said membrane, said apparatus comprising means for determining clearance competency of hemodialyzers including:
  a) measuring means for measuring the composition of a dialyzing solution;
  b) control means for activating a blood displacing pump to circulate blood through the dialyzer;
  c) a detecting means connected to said control means for distinguishing between a priming solution and blood; and
  d) interfacing means connecting the control means to the blood displacing pump for disabling the blood displacing pump when dialyzing solution is not present in the dialysate chamber.

11. The apparatus of claim 10 wherein said measuring means is a conductivity meter.

* * * * *